(12) United States Patent
Piatkowski et al.

(10) Patent No.: US 7,935,514 B2
(45) Date of Patent: May 3, 2011

(54) GENETICALLY MODIFIED YEAST STRAIN

(75) Inventors: Hubert Piatkowski, Chatham (CA); Mark Isaac Schwartz, Woodbridge (CA)

(73) Assignee: GreenField Ethanol Inc., Toronto (CA)

( * ) Notice: Subject to any disclaimer, the term of this patent is extended or adjusted under 35 U.S.C. 154(b) by 0 days.

(21) Appl. No.: 12/271,350

(22) Filed: Nov. 14, 2008

(65) Prior Publication Data

US 2009/0239276 A1  Sep. 24, 2009

Related U.S. Application Data

(60) Provisional application No. 61/038,240, filed on Mar. 20, 2008.

(51) Int. Cl.
*C12N 1/00* (2006.01)
(52) U.S. Cl. .................. 435/255.1; 435/254.1
(58) Field of Classification Search .......... None
See application file for complete search history.

(56) References Cited

U.S. PATENT DOCUMENTS 7,018,829 B1   3/2006  Nielsen et al.

OTHER PUBLICATIONS

Zeyl et al. Experimental studies on ploidy evolution in yeast. FEMS Microbiol Lett. Apr 15, 2004;233(2):187-92.*
Grotakjaer T. et al., "Comparative Metabolic Network Analysis of Two Xylose Fermenting Recombinant Saccharomyces Cerevisiae", Metab Eng., 2005, pp. 437-444, vol. 7-Iusses 5-6, Elsevier Inc.
Moreira Dos Santos M. et al., "Aerobic Physiology of Redox Engineered Saccharomyces Cerevisiae Strains Modified in the Ammonium Assimilation for Increased NADPH Availability", FEMS Yeast Research, 2003, pp. 59-68, vol. 4 Issue 1, Blackwell Publishing Ltd.
Roca C. et al., "Metabolic Engineering of Ammonium Assimilation in Xylose-Fementing Saccharomyces Cerevisiae improves ethanol production", Applied and Environmental Microbiology, Aug. 2003, pp. 4732-4736, vol. 69 No. 8, American Society for Microbiology.
Nissen T.L. et al., "Optimization of Ethanol Production in Saccharomyces Cerevisiae by Metabolic engineering of the ammonium assimilation", Metabolic Engineering, Jan. 2000, pp. 69-77, vol. 2 Issue 1, Academic Press.
Whitehouse, "Towards an Understanding of the Mechanism of Heredity", Edward Arnold Ltd., London, 1965, pp. 327 and 330.
Wilson et al., "Cytology", Reinhold Publishing Corporation, 1961, pp. 174-179.
Swanson, "Cytology and Cytogenetics", MacMillan & Co Ltd., 1963, p. 177.
"Saccharomyces Genome Database FAQ", http://www.yeastgenome.org/SGD-FAQ.html, last updated on website on Mar. 18, 2004.
Hieter et al., "Genetics: Polyploidy—More Is More or Less", Science Magazine, vol. 285, No. 5425, Jul. 9, 1999, pp. 210-211.
Canadian Patent Application 2,641,003 Office Action dated Feb. 28, 2011.

* cited by examiner

*Primary Examiner* — Michele K Joike
(74) *Attorney, Agent, or Firm* — David Conn; Borden Ladner Gervais LLP

(57) ABSTRACT

A polyploid transformed yeast cell comprising a deleted or disrupted GDH1 gene encoding an NADPH-dependent glutamate dehydrogenase. The polyploid yeast cell shows increased production of ethanol and reduced production of glycerol when compared with a control polyploid yeast cell.

1 Claim, 14 Drawing Sheets

ODH200

ODH201

GENETICALLY MODIFIED YEAST STRAIN

This application claims priority from U.S. Ser. No. 61/038,240 filed on Mar. 20, 2008 which is incorporated by reference in its entirety.

FIELD OF THE INVENTION

The present invention relates, in its broad aspect, to genetically modified yeast strains useful for the production of ethanol, in particular to industrial strains of *Saccharomyces cerevisiae* genetically engineered to increase the yield of ethanol from starch fermentation. More particularly, the present invention relates to an improved industrial strain of *Saccharomyces cerevisiae* capable of decreased glycerol production, increased ethanol production and increased tolerance to high concentrations of ethanol.

BACKGROUND OF THE INVENTION

The closest prior art based on the fact that they all appear to disclose genetically modified strains of *S. cerevisiae* having the GDH1 gene at least partially deleted appears to the following:

U.S. Pat. No. 7,018,829 requires only a reduced enzyme activity of a natively present NADPH-dependent glutamate dehydrogenase (as compared to the native level of activity), which, according to a preferred feature, may be achieved by deletion of at least part of at least one native regulatory sequence associated with the native nucleic acid coding for glutamate dehydrogenase or, alternatively, by operably linking the coding sequence of the native glutamate dehydrogenase to a regulatory sequence not natively associated therewith.

A1 Geotkjaer T. et al., Metab. Eng. 2005: 7(5-6), 437-444 ("Comparative metabolic network analysis of two xylose fermenting recombinant *Saccharomyces cerevisiae* strains").

A2 Noreira dos Santos M. et al., FEMS Yeast Res. 2003: 4(1), 59-68 ("Aerobic physiology of redox engineered *Saccharomyces cerevisiae* strains modified in the ammonium assimilation for increased NADPH availability").

A3 Roca C. et al., Appl. Environ. Microbiol. 2003: 69(8), 4732-6 ("Metabolic engineering of ammonium assimilation in xylose-fermenting *Saccharomyces cerevisiae* improves ethanol production").

A4 Nissen T. L. et al., Metab. Eng. 2000: 2(1), 69-77 ("Optimization of ethanol production in *Saccharomyces cerevisiae* by metabolic engineering of the ammonium assimilation") discloses a genetically manipulated *S. cerevisiae* strain having the GDH1 gene deleted and two other genes in the glutamate synthetic pathway overexpressed. It further seems that all the strains disclosed by the above documents (which all appear to derive from one research group) are characterized by an increased ethanol and reduced glycerol production, which effects seem to be attributed, at least in part, to the deletion of GDH1 gene.

All the genetically modified *S. cerevisiae* strains disclosed by papers A1 through A4 and U.S. Pat. No. 7,018,829 seem to include genetic modifications additional to the deletion of GDH1 gene (those disclosed in papers A1 and A3, for example, are xylose-fermenting strains comprising heterologous genes making possible xylose to ethanol conversion, a capacity native strains of *S. cerevisiae* lack). They also all involve laboratory rather than industrial strains of yeast. In passing it should be noted that laboratory strains of yeast are mainly haploid with a single complement of genetic material whereas industrial yeasts are very often polyploid having more than one complement of genetic material which makes them difficult and unpredictable to work with.

It is, therefore, still desirable simply to provide an improved industrial strain of *Saccharomyces cerevisiae* capable of decreased glycerol production, increased ethanol production and increased tolerance to high concentrations of ethanol.

SUMMARY OF THE INVENTION

It is an object of the present invention to obviate or mitigate at least one disadvantage of previous developments and to provide an improved industrial strain of *Saccharomyces cerevisiae* capable of decreased glycerol production, increased ethanol production and increased tolerance to high concentrations of ethanol.

In a first aspect, the present invention provides a polyploid transformed yeast cell comprising a deleted or disrupted GDH1 gene encoding an NADPH-dependent glutamate dehydrogenase, said polyploid yeast cell showing increased production of ethanol and reduced production of glycerol when compared with a control polyploid yeast cell. In a preferred embodiment the polyploid yeast cell carries the designation 213A.

In a further embodiment, there is provided a method for preparing a polyploid transformed yeast cell showing increased production of ethanol and reduced production of glycerol when compared with a control polyploid yeast cell which method comprises disrupting or deleting alleles of a GDH1 gene present in a polyploid yeast cell.

In a further aspect, the present invention provides a method for producing ethanol with reduced production of glycerol by-product which method comprises culturing the polyploid transformed yeast cell of the invention.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Figure 1:
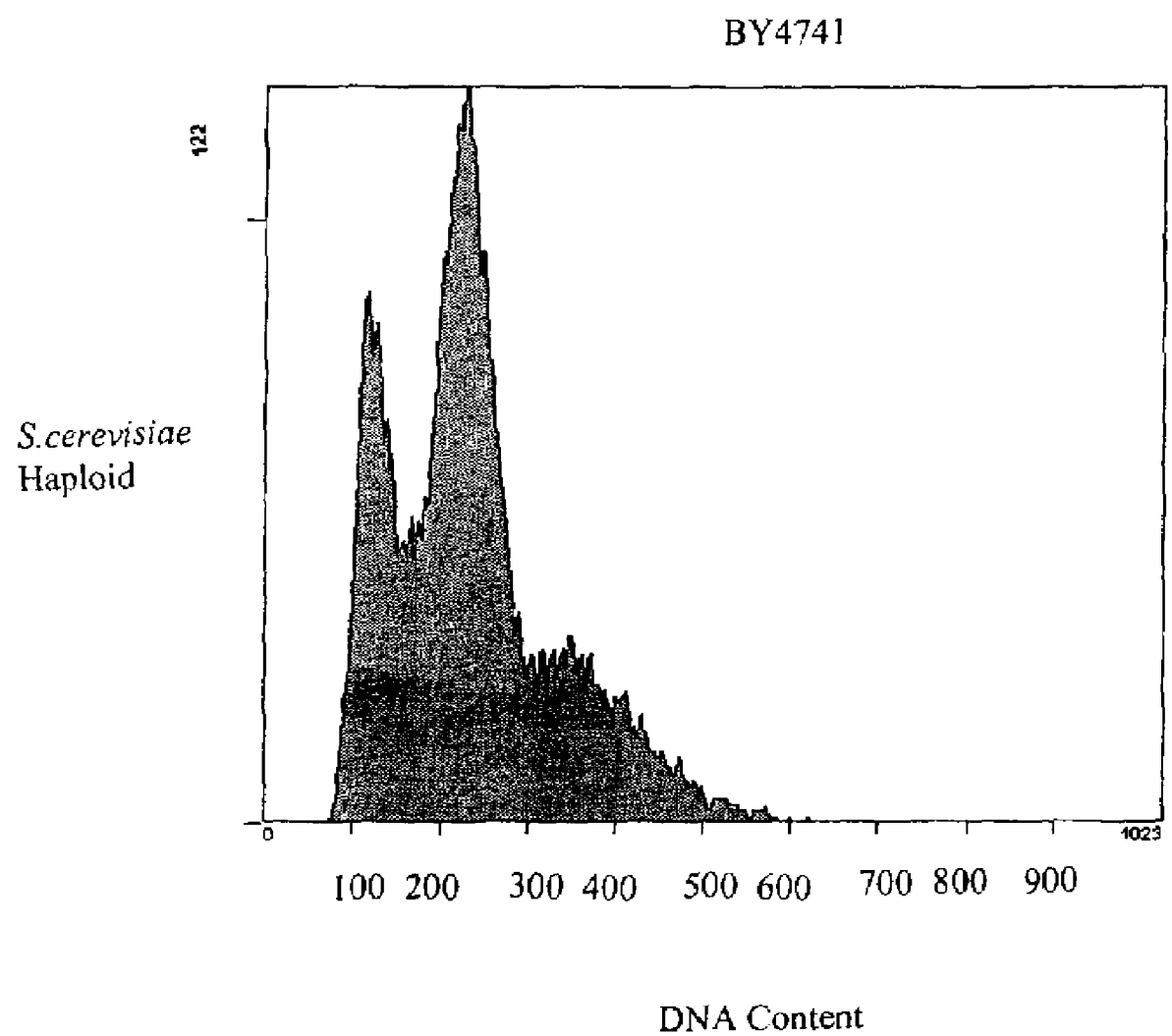
FIG. 1 is a FACS analysis of a haploid strain of *Saccharomyces cerevisiae*.
Figure 2:
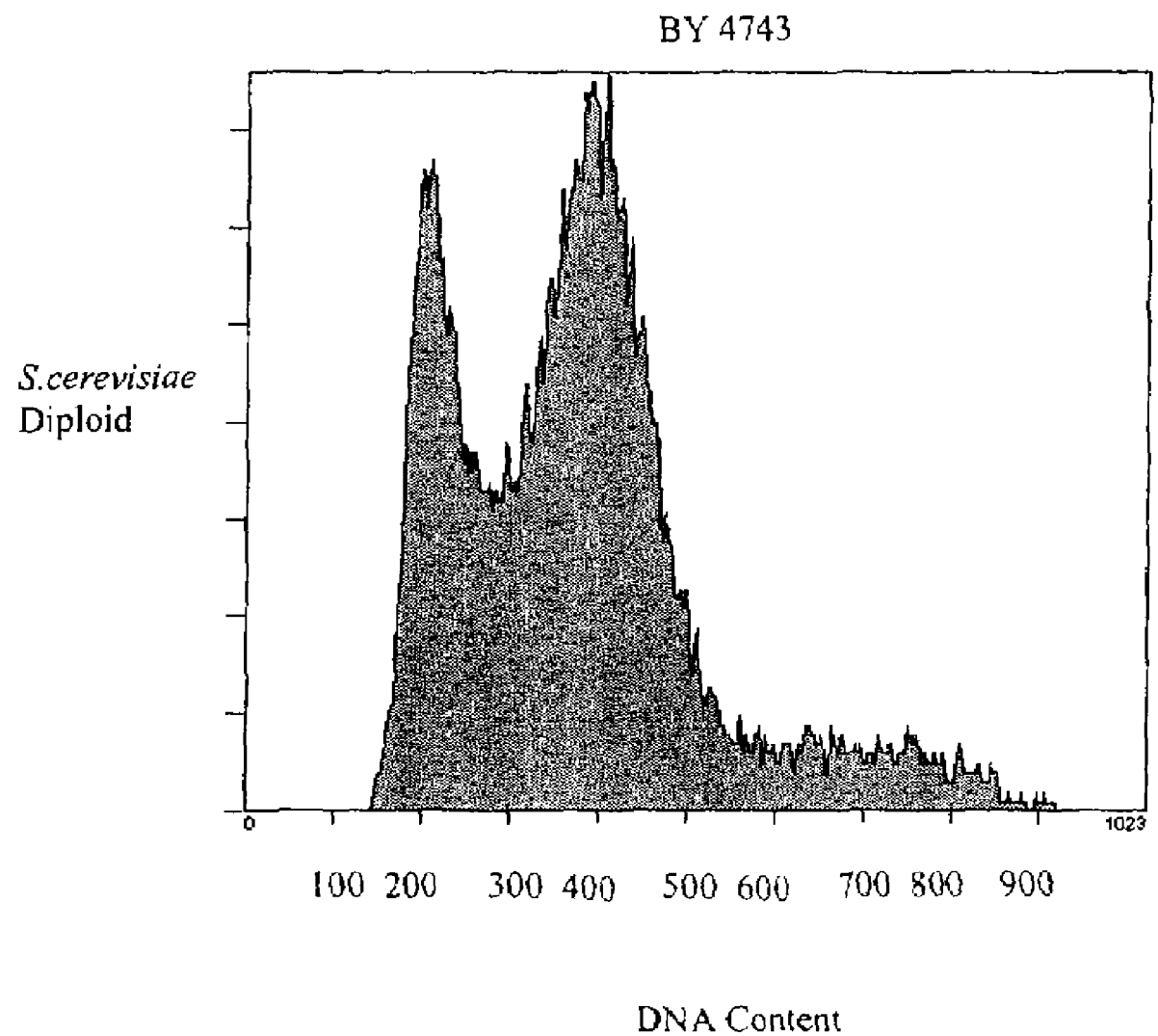
FIG. 2 is a FACS analysis of a diploid strain of *Saccharomyces cerevisiae*.
Figure 3:
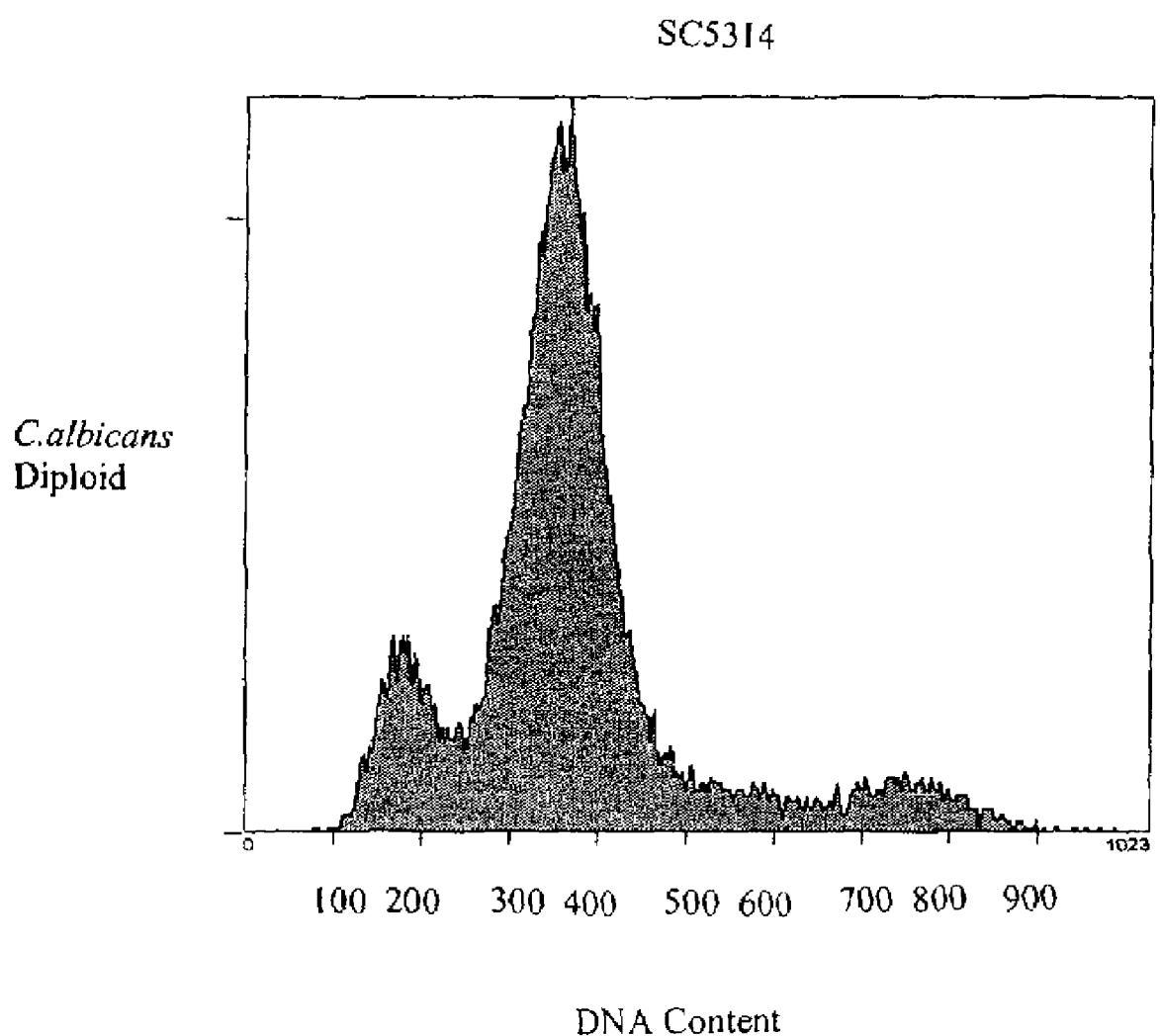
FIG. 3 is a FACS analysis of a diploid strain of *Candida albicans*.
Figure 4:
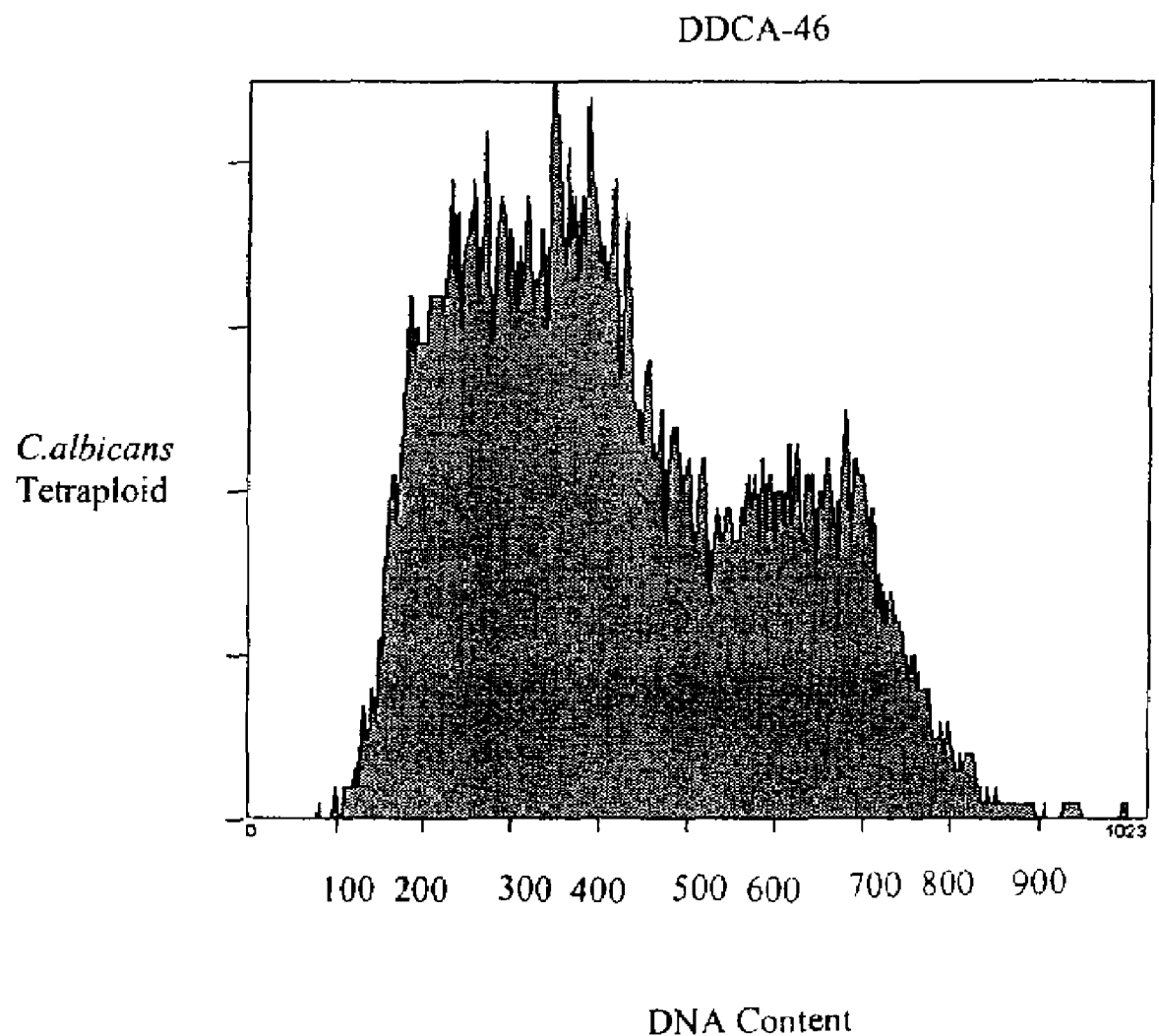
FIG. 4 is a FACS analysis of a tetraploid strain of *Candida albicans*.
Figure 5:
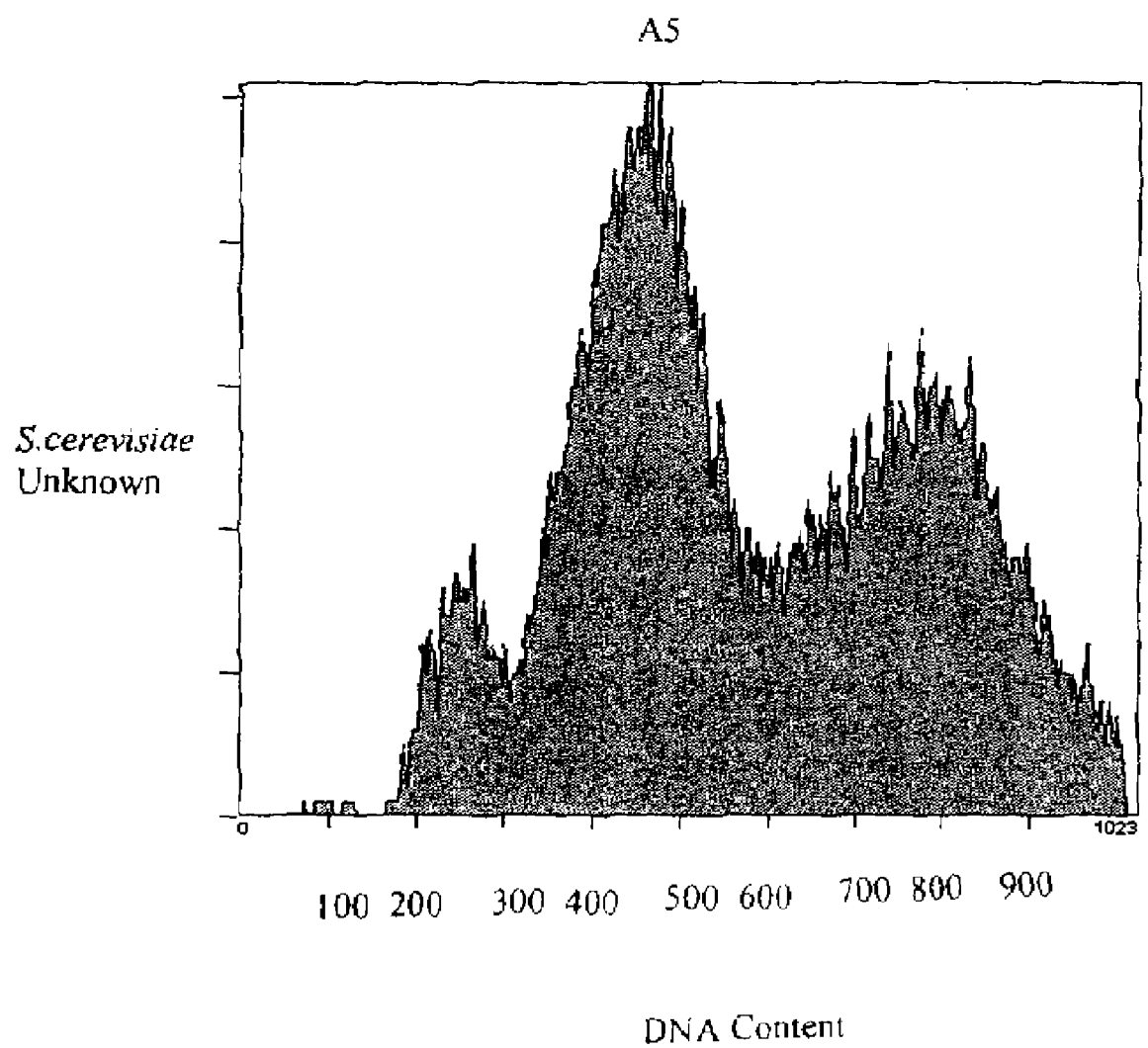
FIG. 5 is a FACS analysis of the A5 strain of *Saccharomyces cerevisiae* used in making yeast cells of the invention.

The overall objective is to decrease the amount of glycerol being produced by yeast. Glycerol is a waste by-product of fermentation which is produced by yeast on a continuous basis, and since it brings no financial benefit, the decrease in its production should result in ethanol yield increase and overall better performance.

Glycerol is a by-product created during yeast fermentation. The importance of glycerol in yeast fermentation has to do with yeast's ability to re-oxidize the surplus of NADH which is formed during anaerobic fermentation, and maintaining a redox balance under anaerobic conditions. NADH is formed in cell synthesis reactions, most notably amino acid synthesis and other biomass synthesis. The NADH production must be balanced by a mechanism in which NADH is re-oxidized to NAD+ in order to avoid a serious imbalance in the NAD+/NADH ratio. Under anaerobic conditions the respiratory chain is not functioning, and instead, the NADH is re-oxidized to NAD+ by the formation of glycerol, with the synthesis of 1 mol of glycerol resulting in re-oxidizing 1 mol of NADH. Glycerol is also formed when yeast is grown in high osmotic stress conditions. In this case glycerol acts as an osmoregulator and substantial amounts of glycerol can be produced. The glycerol accumulates inside the cell and effectively protects the cell from lysis.

Specific objectives deal with the elimination of glycerol as a product of fermentation. Theoretically, if all the glycerol production can be halted, the overall production of ethanol has the potential to be increased by up to 8% based on current lab results. As such, even the elimination of small percentage of the produced glycerol will result in a significant increase in production of ethanol. At the same time, the overall yield of ethanol per bushel of corn will also increase because of more efficient fermentation.

The technical objective is to modify a strain of *Saccharomyces cerevisiae* yeast to enable it to re-oxidize NADH using an alternative pathway from that used for glycerol production. Based on past published research which has been carried out in regards to glycerol production, we believe it should be possible to reduce glycerol production by up to 40% while at the same time increasing ethanol production by 3%.

Generally, the invention provides, a wild (native, genetically unmodified) strain of *S. cerevisiae* (designated as "A5" strain) which was first isolated from industrial sources after a 5-month fermentation period. This strain was then genetically modified by deletion/disruption of GDH1 gene encoding an NAPDH-dependent glutamate dehydrogenase, an enzyme synthesizing glutamate from ammonia and alpha-ketoglutarate. This modification resulted in a strain designated "213A", characterized by an increased production of ethanol and reduced production of glycerol. These two phenotypic characteristics, only indirectly related to the genotypic trait of the gene GDH1 being deleted or disrupted (the gene in question is not directly involved in the synthesis of either glycerol or ethanol), make the strain more suitable for the production of ethanol by fermentation of starch-based substrates. For the purpose of comparison with other genetically modified yeast strains, it is important to note that the deletion/disruption of GDH1 gene is the only genetic modification of the genome of the native strain A5 and that no heterologous (exogenous) DNA sequences were entered into its genome.

EXAMPLE 1

Determination of Strain Ploidy

Strain A5 was propagated on a Yeast Peptone Dextrose (YPD) plate at 30° C. and grew well.

The ploidy of the A5 strain was estimated using FACS analysis on cells stained with propidium iodide. The A5 strain was compared to haploid (BY4741) and diploid (BY4743) *Saccharomyces cerevisiae* strains and to diploid (SC5314) and tetraploid (DDCA-46) *Candida albicans* strains. In flow cytometry the DNA content of cells is measured by determining the relative fluorescence intensities. The channel number is correlated with the intensity of fluorescence, that is, in proportion to the channel number the DNA content in the cells increases.

FIGS. 1-5 show the comparison of haploid, diploid and tetraploid strains to the A5 strain of unknown ploidy. The two main peaks in each sample should represent the pre and post-replicative DNA contents (1 and 2C values). These are 100 and 200 for the haploid *S. cerevisiae*, 200 and 400 for the diploid *S. cerevisiae*, about 175 and 350 for the diploid *C. albicans*, and 350 and 700 for the tetraploid *C. albicans*. The values for the unknown A5 strain are about 450 and 800, so the DNA content of the A5 strain has values closest to that of an *S. cerevisiae* tetraploid.

EXAMPLE 2

Disruption of GDH1—1$^{st}$ Allele

Strain A5 was tested for sensitivity to G418 and phleomycin. The strain was sensitive to the standard concentration of G418 used for yeast (200 µg/ml), and sensitive to phleomycin but at a higher concentration (50 µg/ml) than recommended for *Saccharomyces cerevisiae* (10 µg/ml).

Figure 6:
FIG. 6 shows part of the plasmid pUG6.

100 mer oligos (ODH200 & ODH201) were designed with an 80 bp homology to the upstream or downstream flanking region of the GDH1 gene and a 20 bp homology flanking the loxPKanloxP cassette in the plasmid pUG6 (see FIG. 6).

Figure 7:
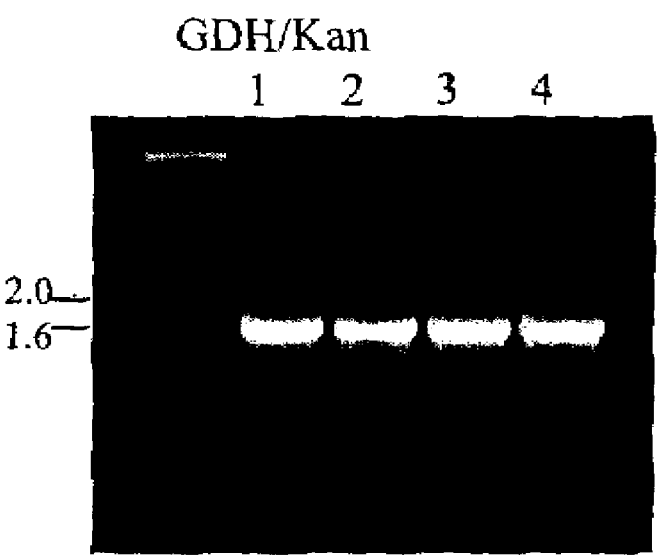
FIG. 7 shows four separate PCR performed using ODH200 and 201 on the pUG6 plasmid with rTaq.

Four separate PCR reactions were performed using ODH200 and 201 on the pUG6 plasmid with rTaq (see FIG. 7).

The 1.8 kb PCR products (GDH1/Kan) were cleaned on Quiagen PCR columns. 50 ng of each product was used for a sequencing run with primers designed overlapping and internal of the GDH1/Kan cassette (ODH202, 203, 204, 205).

The sequence of the oligos and product were verified, however 15 more PCR reactions were done to yield the amount of DNA required for the transformation.

5-10 µg of the cassette DNA were used for the transformation (LiOAc protocol) of the CAI strain A5, and control lab strains BY4741 (haploid) and BY4743 (diploid). The transformed cells were plated to YPD plates and after 2 days were replica plated to G418 plates.

Figure 8:
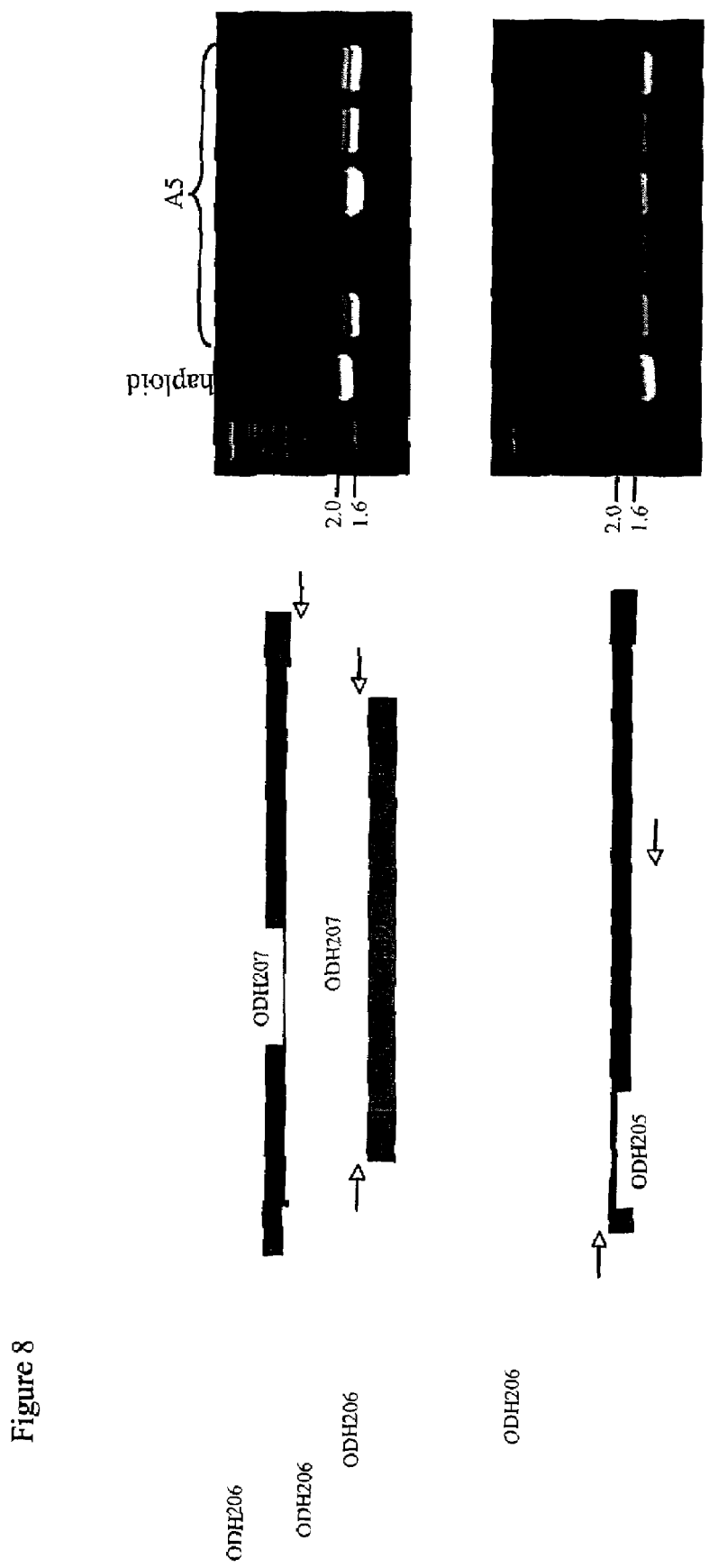
FIG. 8 shows blots demonstrating disruption of at least one GDH1 allele.

Colonies resistant to G418 were confirmed for the disruption of GDH1 using colony PCR and Expand Long Enzyme with oligos flanking the disruption cassette (ODH206 & 207). These oligos should give a product of 1.8 kb (disrupted allele) in the haploid control and two bands of 1.8 kb and 1.6 kb (wild type allele) in the A5 strain. However, since this is a competitive PCR reaction between the wild type and disrupted alleles quite often only the smaller band representing the wild type allele is produced, therefore another PCR reaction with ODH206 and an oligo inside the Kan marker (ODH205) is also done. As shown in FIG. 8 all of the A5 transformants tested were positive for disruption of at least one allele of GDH1.

Three of the A5 transformants positive for disruption of the first allele were chosen for transformation with the GAL1-Cre-Phleomycin plasmid (pSH65). Induction of the Cre recombinase will increase the frequency of recombination between the loxP sites to loop out the kanamycin marker for further disruptions.

pSH65 was transformed using a quick transformation protocol; transformed cells were plated on YPD and after one day replica plated to phleomycin (50 µg/ml) plates. Several of the phleomycin resistant colonies were streaked out again on phleomycin plates and then replica plated to G418 plates to look for colonies that were G418 sensitive and hence had lost the kanamycin marker. Note that we did not induce the Cre recombinase with galactose as it had been reported that there is residual activity of the GAL1 promoter in the presence of glucose, and this turned out to be true. The colonies that were phleomycin resistant and G418 sensitive were then confirmed by colony PCR using oligos ODH206 and 207 for loss of the kanamycin marker.

Figure 9:
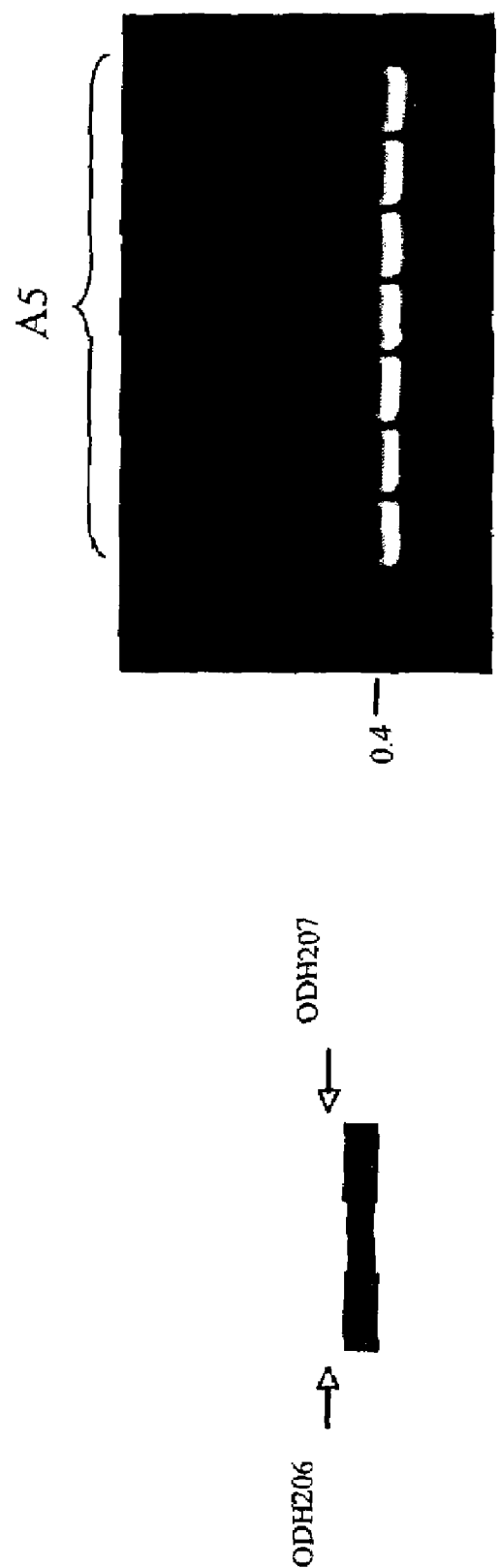
FIG. 9 shows "looping out" of the kanamycin marker.

As shown in FIG. 9 all of the transformants tested had looped out the kanamycin marker.

Kan— colonies were streaked out on YPD plates and the next day replica plated to YPD+phleomycin to look for colonies that were now sensitive to phleomycin because they had lost the Cre plasmid. In theory the Cre plasmid can be left in the strain and further disruptions carried out but we were concerned that because of its residual activity in glucose it might interfere with further disruptions using the Kanamycin marker.

We took two of the first allele disruptions that are Kan–, Cre– and also two that are Kan–, Cre+ and proceeded with the disruption of the second GDH1 allele.

EXAMPLE 3

Disruption of GDH1—2$^{nd}$ Allele

Kan$^-$, Cre$^+$ and Kan$^-$, Cre$^-$ strains disrupted for the 1$^{st}$ allele of GDH1 were transformed with 5-10 µg of the cassette DNA, using the same cassette as the first disruption. The transformed cells were plated to YPD plates and the next day replica plated to G418. Colonies resistant to G418 were tested for the disruption of the second allele of GDH1 using colony PCR with ODH206 & 207, as previously described. If the second allele is disrupted these oligos should give products of 0.4 kb for the disrupted 1$^{st}$ allele (deleted gene replaced with the single loxP region), of 1.6 kb for the wild type allele and of 1.8 kb for the disrupted 2$^{nd}$ allele (Kan+ loxP). In the case where the cassette has integrated back at the first disrupted allele then only the products for the WT and Kan+ loxP would be present. In either case, because this is a competitive PCR it is possible we would not see all the bands produced as smaller bands are preferentially amplified.

Figure 10:
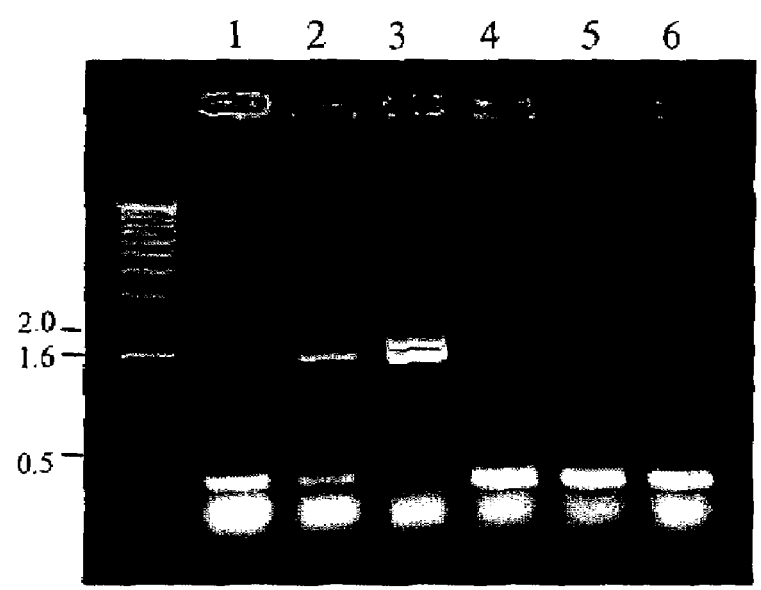
FIG. 10 shows results of disruption of the second GDH1 allele.

As shown in FIG. 10, of the six transformants checked by PCR only #3 appears to have the second introduced cassette integrated back at the site of the 1$^{st}$ disrupted allele (no loxP band, meaning the disrupted allele is missing but a Kan+ band, showing the second cassette had integrated). Of the remaining samples the Kan+ band is not clear and only #1 and #2 show a wild type band.

Figure 11:
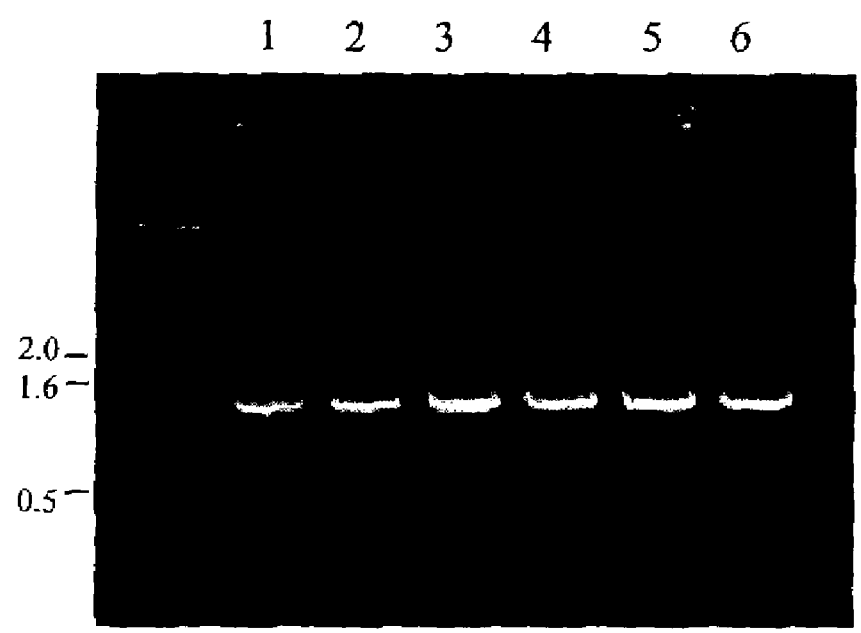
FIG. 11 provides evidence that transformants have two disrupted alleles of GDH1.

To confirm that all of the transformants have a Kan+ allele a PCR was done using oligos ODH205 & 206 (oligos previously described) that should give a product of 1.4 kb. As shown in FIG. 11 all the transformants have the Kan+ allele. This means that all of the transformants (with the exception of #3) should have two disrupted alleles of GDH1; in the case of #3 the two independent transformations targeted the same allele.

We found it curious that, as mentioned above, we did not see a product for the wild type band in sample #'s 4, 5 and 6.

Because of the presumed tetraploid nature of the A5 strain, two successful rounds of disruption should have left 2 copies of the wild-type gene. However, the PCR analysis suggested that all the GDH1 alleles were disrupted. To check if they had the expected wild-type band, but it was just not visible because of the competitive PCR, an oligo was designed inside the wild type GDH1 gene (ODH208).

Figure 12:
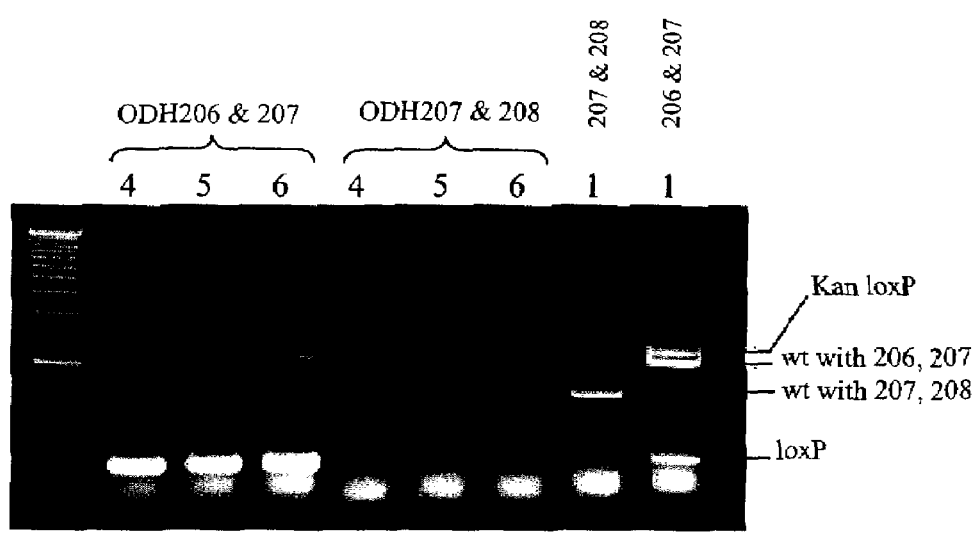
FIG. 12 and FIG. 13 provide evidence of full disruption of the GDH1 gene in strain A5.

FIG. 12 shows PCR with oligos ODH207 & 208 on sample #1 as a positive control (the wild type band was present in this transformant) and on the samples in question, #'s 4, 5 and 6. PCR was also repeated on these samples with oligos ODH206 & 207 to show that PCR can be successful with the DNA from these transformants. We can see clearly that there is no wild type band in #'s 4, 5 and 6. This suggests that we have a full disruption of the GDH1 gene in strain A5.

Figure 13:
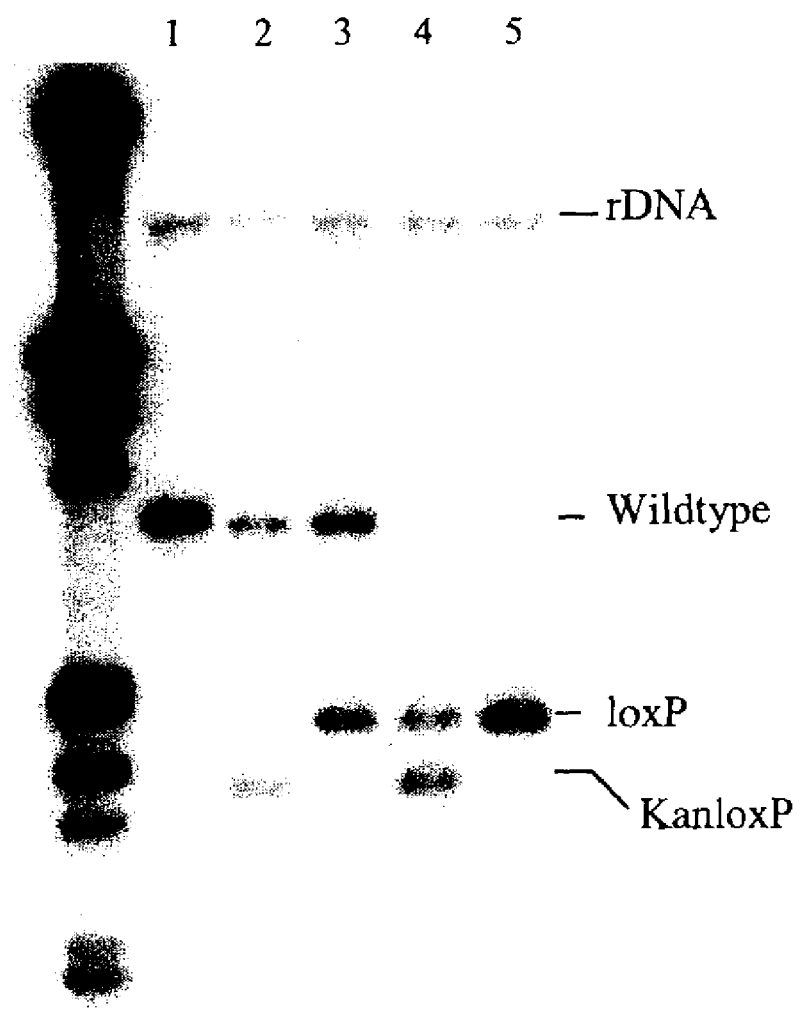

Because we were surprised to see that we had succeeded in removing all of the wild-type GDH1 alleles in just two steps, we did a Southern blot to confirm the PCR results. In the Southern we used DNA from strains at each step of the disruption, these are:

Lane 1—A5 wild-type strain from Commercial Alcohols Inc.
Lane 2—A5DH-113, 1$^{st}$ disrupted allele Kan+
Lane 3—A5DH-113a, 1$^{st}$ disrupted allele Kan$^-$
Lane 4—A5DH-213, 2$^{nd}$ disrupted allele Kan+
Lane 5—A5DH-213a, 2$^{nd}$ disrupted allele Kan$^-$ As shown in the Southern blot in FIG. 13 there is no wild type GDH1 band in lanes 4 and 5. This confirms that we have a complete disruption of GDH1.

A second point that is evident in the Southern is that the intensities of the two bands within one lane that represent the different alleles of GDH1 are the same. One interpretation of this result is that the A5 strain is diploid for GDH1 even though the results of our FACS analysis of DNA content showed the strain was a tetraploid. The ability to remove all GDH1 genes with only two rounds of disruption is also compatible with there being a diploid constitution for GDH1 in strain A5.

Because the FACS analysis established that A5 behaved as a tetraploid, while mutation of GDH1 generated knock-outs after only two rounds of disruption, we did an independent test of the ploidy of the A5 strain.

Figure 14:
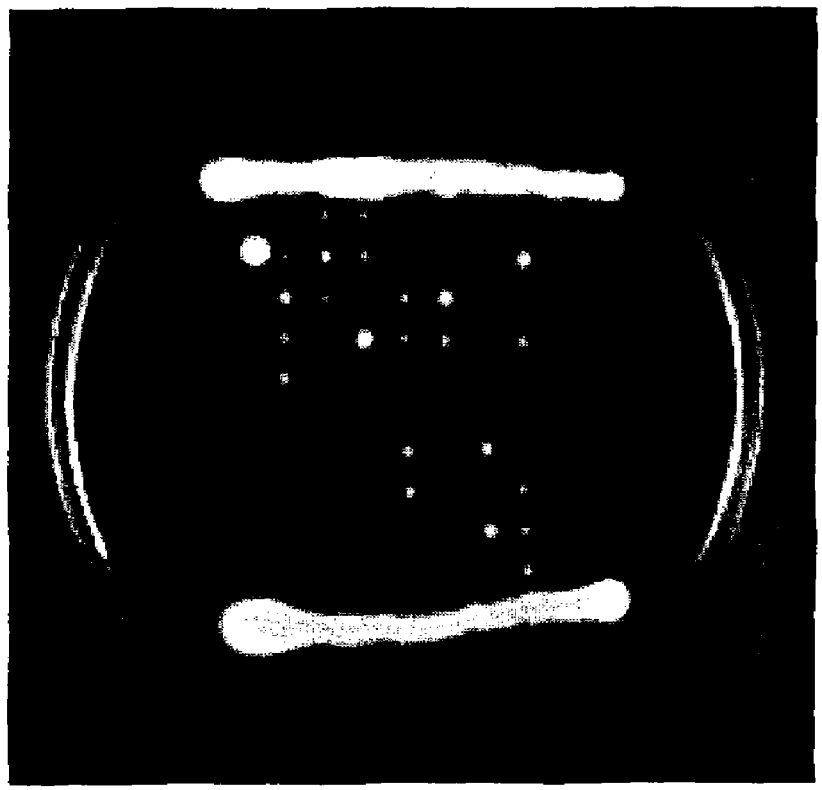
FIG. 14 provides evidence of even ploidy of 4 or more—most likely tetraploidy.

If the A5 strain was truly tetraploid, the strain should be able to undergo sporulation to generate diploid meiotic products. Therefore we induced sporulation in the A5 strain, and the meiotic products were separated by micromanipulation and allowed to grow to form colonies. This is shown in FIG. 14. Spore viability was adequate, with one complete tetrad and several three-spored tetrads, suggesting that the strain was likely either diploid or tetraploid. If the A5 strain were diploid, then these viable meiotic products would all be non-sporulating and would be mating competent, with half the spores responsive to the mating factor α-factor. If the A5 strain were tetraploid, then few of the resulting spores would be responsive to mating factor, and many of the spores would themselves be capable of sporulation. This latter result was obtained; from 25 spores tested only 3 showed response to mating factor, and 7 showed sporulation capacity. Therefore the genetic results are compatible only with an even ploidy of 4 or greater, confirming tetraploidy as the most likely genomic constitution of strain A5.

Strains Developed.

A5/dh113a—GDH1/gdh1Δ::loxP. Parent is CAI wild-type strain A5.

A5/dh213a—gdh1Δ::loxP/gdh1Δ::loxP. Parent is A5/dh113a

| Protocols used in Commercial Alcohols Project | | | |
|---|---|---|---|
| PCR Protocols | | | |
| PCR from plasmid | | Program | |
| Plasmid DNA | 1 µl | 96° C. - 2 min | |
| for. oligo(20 µm) | 1 µl | | |
| rev. oligo(20 µm) | 1 µl | 94° C. - 30 sec | |
| rTaq buffer | 5 µl | 55° C. - 30 sec | 30 cycles |
| 1.25 mM dNTP mix | 8 µl | 72° C. - 2.5 min | |
| Amersham rTaq | 0.5 µl | | |
| $H_2O$ | 33.5 µl | 72° C. - 5 min | |
| Total | 50 µl | 4° C. - hold | |

Colony PCR
    Touch a colony or cell pellet with a sterile pipette tip.
    Rinse the tip with 10 µl Zymolyase Solution (2.5 mg/ml Zymolyase (ICN), 1.2M sorbitol, 0.1M Na phosphate pH7.4) by pipetting up and down several times.
    Incubate for 30-60 min @ 37° C.
These cells can now be frozen or used immediately for PCR.

| | | Program | |
|---|---|---|---|
| Cells | 2 µl | | |
| 10 mM dNTP mix | 1 µl | | |
| for. oligo(20 µm) | 2.5 µl | 94° C. - 4 min | |
| rev. oligo(20 µm) | 2.5 µl | | |
| Expand Buf. 1 | 5 µl | 94° C. - 30 sec | |
| $H_2O$ | 36.25 | 45° C. - 30 sec | 30 cycles |
| Exp. long enz. | 0.75 | 68° C. - 2 min | |
| Total | 50 µl | | |
| | | 68° C. - 7 min | |
| | | 4° C. - hold | |

Transformation Protocol (Modified from Guldener U. et al. Nucleic Acids Research, 1996, Vol. 24, No. 13 2519-2524) for PCR Based Disruption with Kanamycin Marker.
    Dilute overnight culture to an O.D.$_{600}$ of 0.2 and grow to 0.7-1.0 (≈4 h) in 50 ml YPD
    Spin down @ 4000 rpm 5 min
    resuspend in 10 ml $H_2O$
    Spin down
    resuspend in 1 ml $H_2O$
    Spin down 5000 rpm 1 min
    resuspend in 1.5 ml of Lite (make 5 ml. fresh –500 µl. TE, 500 µl. 1M LiOAc, 4 ml. $H_2O$)
    Spin, resuspend in 200 µl Lite
    Mix (do not vortex) 5-10 µg DNA (12 µl) with 50 µg SSDNA (5 µl—boiled for 2 min. and chilled on ice) and 50 µl of cells.
    Add 300 µl of 40% PEG (800 µl 50% PEG, 100 µl TE, 100 µl 1M LiOAc) mix (don't vortex)
    Incubate for 30 min @ 30° C. with constant agitation
    Incubate 15 min @ 42° C.
    Add 800 µl $H_2O$ mix and spin @ 13,000 rpm for 10 sec
    Resuspend cells in 200 µl YPD (no vortexing)
    Plate on two YPD plates and leave at 30° C. overnight
    Replica to selective plate (i.e. G418 for Kanamycin) and leave at 30° C. overnight
    If background it too high then replica plate another time.
Quick and Dirty Transformation Protocol
    (based on Chen et al. Current Genetics (1992) 21:83-84
Spin down 0.3 ml of stationary cells (overnight culture or older; 1 wk old transform well)
Suspend in 0.1 ml OSB (one-step buffer)
Add transforming DNA (up to 10 µl, 2 µg is more than enough, see note below) Vortex to mix
Incubate 30-60 min at 45° C. for Sacch; at 43.5° C. for *Candida* (can do this in PCR machine or waterbath)
Plate on two YPD plates and grow overnight at 30° C.
Next day replica plate to selective media (i.e. for Kanamycin or Phleomycin)
If after one day of growth there is too much background then do another replica plate.
NOTE:
If using this method for transformation of a PCR product with short homology:
    Use 6-10 µg DNA
For 1 ml OSB:
0.2 ml 1M LiOAc/in TE
0.8 ml 50% PEG 4000 (now 3400)
15 mg DTT (dithiothreitol) poder (0.1M)
25 µl SSDNA (10 mg/ml)
This solution should be made up fresh before use. 2.5 µl SSDNA can be added to each transformation tube instead of 25 µl in the whole mix.
Media Used in the Project
YPD liquid media
1% Yeast extract
2% Bacto-peptone
2% Dextrose
add 2% Agar for solid media
Media for Kanamycin Resistance
Geneticin=antibiotic G418 (Gibco)
Make a stock of 50 mg/ml in $H_2O$ and filter sterilize (do not autoclave), stock should be kept at –20° C.
Use 4 ml/l of YPD media for a final concentration of 200 µg/ml
Media for Phleomycin Resistance
Phleomycin (Invivogen)
Resuspend in $H_2O$ or Hepes buffer (pH7.5) at a concentration of 20 mg/ml and filter sterilize (do not autoclave), stock can be kept in the fridge short-term and at –20° C. long-term.
Use 2.5 ml/l of YPD media for a final concentration of 50 µg/ml
    Sequences
Sequences for GDH1, GLN1, GLT1, and PGK1 were obtained from the *Saccharomyces* Genome Database (SGD).
Sequence and map of the pUG6 plasmid were obtained from Euroscarf.
The pSH65 map is not available on the Euroscarf site, however a similar map (pSH63) is available.
The pBluescript (pBSKS+) map and sequence were obtained from Stratagene.
    Oligos used in the Project
Underlined is pUG6 sequence ODH200 (forward oligo for PCR of GDH1 disruption cassette)
(SEQ ID NO: 1)
5' TCT TAT AGC ATT GAA AGT TGC TTG ATA CGT ACT ATC GCA TTA TTC TAA TAT AAC AGT TAG GAG ACC AAA AAG AAA AAG AA<u>C TTC G TAC GCT GCA GGT CGA</u> 3'

-continued

ODH201 (reverse oligo for PCR of GDH1 disruption
cassette)
                                        (SEQ ID NO: 2)
5' TAT CTC ATT ATC TAT CTA AGT TAT TTA AAA AAA AGA
AAG AAC TTT TTA TGA ACT TTC CTC TTT TCT TTC TTT
TAG ACT ATC CAC TAG TGG ATC TGA TAT CA 3'

ODH206 (forward oligo flanking disruption cassette
for detection of GDH1 disruption)
                                        (SEQ ID NO: 3)
5' GCG TTT ACC CAT TTT ATA TTC 3'

ODH207 (reverse oligo flanking disruption cassette
for detection of GDH1 disruption)
                                        (SEQ ID NO: 4)
5' CTC CCG ATA ATC AAT TTT CTT 3'

ODH208 (forward oligo inside of the orf of GDH1
for detection of the wild-type allele)
                                        (SEQ ID NO: 5)
5' GTG TTG GTG GTC GTG AAA TTG 3'

ODH213 (forward oligo for GDH1 Southern probe)
                                        (SEQ ID NO: 6)
5' cgg aat cgt aac gca att aat 3'

ODH214 (reverse oligo for GDH1 Southern probe)
                                        (SEQ ID NO: 7)
5' aaa gcc gct tct gaa tcc atc 3'

ODH215 (forward oligo to PCR PGK1 promoter)
                                        (SEQ ID NO: 8)
5' gac tag tag ggc cag aaa aag gaa gtg t 3'

ODH216 (reverse oligo to PCR PGK1 promoter)
                                        (SEQ ID NO: 9)
5' cgg gat cct gtt tta tat ttg ttg taa a 3'

Summarized Results 33 semi-continuous trials have been run with the modified yeast strains (propagating from previous generations) with the following results indicating that the modifications did enhance the yeast. The following table is a summary of those results (averages per strain tested). Strain A5 is the original isolated strain following 6 months of fermentation. Strain 213A is the original modified strain. Strain 213 A-# are the selected colonies from micro plates based on colony size.

TABLE 1

| Strain | Glycerol (g/L) | Ethanol (% wt/vol) | Glycerol Change | Ethanol change |
|---|---|---|---|---|
| A5 (mother) | 9.23 | 12.28 | −2.01% | 1.08% |
| 213A | 8.38 | 12.52 | −11.31% | 3.01% |
| 213A-1 | 8.43 | 12.53 | −10.82% | 3.08% |
| 213A-2 | 8.37 | 12.51 | −11.43% | 2.93% |
| 213A-3 | 8.33 | 12.51 | −12.01% | 2.91% |
| 213A-4 | 8.32 | 12.50 | −12.04% | 2.83% |

Note that the changes to the genome of 213A are permanent. After months of testing, the modifications were not reversed and the yeast continues to produce lower amounts of glycerol as compared to its parent strain. No genetic material from a different organism was inserted into the genome of the yeast. The deletion cassettes were designed in such a way to excise any antibiotic resistance genes from the sites of interest following the genetic modifications. This has implications for approvals for use as it makes this that much easier. Strain 213A is identical to the mother strain in its resistance to antibiotics such as cycloheximide. It will not grow at levels over 3 ppm. There are no antibiotic markers in the genome. *Saccharomyces cerevisiae* strain 213A has been deposited at the International Depository Authority of Canada (IDAC), National Microbiology Laboratory, Public Health Agency of Canada, 1015 Arlington Street, Winnipeg, Canada R3E 3R2 on Sep. 26, 2007 with Accession Number 260907-1. The deposit of the deposited strain has been made pursuant to the terms of the Budapest Treaty. The deposited strain will be irrevocably and without restriction or condition released to the public on the issuance of a patent. The deposited strain is provided merely as a convenience as is not an admission that a deposit is required for enablement.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A polyploid yeast cell carrying the designation 213A (IDAC Accession Number 260907-1).

* * * * *

UNITED STATES PATENT AND TRADEMARK OFFICE
CERTIFICATE OF CORRECTION

| | | |
|---|---|---|
| PATENT NO. | : 7,935,514 B2 | Page 1 of 1 |
| APPLICATION NO. | : 12/271350 | |
| DATED | : May 3, 2011 | |
| INVENTOR(S) | : Hubert Piatkowski et al. | |

It is certified that error appears in the above-identified patent and that said Letters Patent is hereby corrected as shown below:

Column 6, line 64 and line 66, delete "IoxP" and insert therefor --loxP--.

Signed and Sealed this
Twenty-third Day of August, 2011

David J. Kappos
*Director of the United States Patent and Trademark Office*

SEQUENCE LISTING

<160> NUMBER OF SEQ ID NOS: 9

<210> SEQ ID NO 1
<211> LENGTH: 100
<212> TYPE: DNA
<213> ORGANISM: Artificial Sequence
<220> FEATURE:
<223> OTHER INFORMATION: ODH200 (forward oligo for PCR of GDH1
      disruption cassette)

<400> SEQUENCE: 1
tcttatagca ttgaaagttg cttgatacgt actatcgcat tattctaata taacagttag      60
gagaccaaaa agaaaaagaa cttcgtacgc tgcaggtcga                           100

<210> SEQ ID NO 2
<211> LENGTH: 101
<212> TYPE: DNA
<213> ORGANISM: Artificial Sequence
<220> FEATURE:
<223> OTHER INFORMATION: ODH201 (reverse oligo for PCR of GDH1
      disruption cassette)

<400> SEQUENCE: 2

```
tatctcatta tctatctaag ttatttaaaa aaaagaaaga acttttatg aactttcctc    60 ttttctttct tttagactat ccactagtgg atctgatatc a                     101

<210> SEQ ID NO 3
<211> LENGTH: 21
<212> TYPE: DNA
<213> ORGANISM: Artificial Sequence
<220> FEATURE:
<223> OTHER INFORMATION: ODH206 (forward oligo flanking disruption
      cassette for detection of GDH1 disruption)

<400> SEQUENCE: 3
gcgtttaccc attttatatt c                                            21

<210> SEQ ID NO 4
<211> LENGTH: 21
<212> TYPE: DNA
<213> ORGANISM: Artificial Sequence
<220> FEATURE:
<223> OTHER INFORMATION: ODH207 (reverse oligo flanking disruption
      cassette for detection of GDH1 disruption)

<400> SEQUENCE: 4
ctcccgataa tcaattttct t                                            21

<210> SEQ ID NO 5
<211> LENGTH: 21
<212> TYPE: DNA
<213> ORGANISM: Artificial Sequence
<220> FEATURE:
<223> OTHER INFORMATION: ODH208 (forward oligo inside of the orf of
      GDH1 for detection of the wild-type allele)

<400> SEQUENCE: 5
gtgttggtgg tcgtgaaatt g                                            21

<210> SEQ ID NO 6
<211> LENGTH: 21
<212> TYPE: DNA
<213> ORGANISM: Artificial Sequence
<220> FEATURE:
<223> OTHER INFORMATION: ODH213 (forward oligo for GDH1 Southern
      probe)

<400> SEQUENCE: 6
cggaatcgta acgcaattaa t                                            21

<210> SEQ ID NO 7
<211> LENGTH: 21
<212> TYPE: DNA
<213> ORGANISM: Artificial Sequence
<220> FEATURE:
<223> OTHER INFORMATION: ODH214 (reverse oligo for GDH1 Southern
      probe)

<400> SEQUENCE: 7
aaagccgctt ctgaatccat c                                            21

<210> SEQ ID NO 8
<211> LENGTH: 28
<212> TYPE: DNA
<213> ORGANISM: Artificial Sequence
<220> FEATURE:
<223> OTHER INFORMATION: ODH215 (forward oligo to PCR PGK1 promoter)

<400> SEQUENCE: 8
```

```
gactagtagg gccagaaaaa ggaagtgt                                              28

<210> SEQ ID NO 9
<211> LENGTH: 28
<212> TYPE: DNA
<213> ORGANISM: Artificial Sequence
<220> FEATURE:
<223> OTHER INFORMATION: ODH216 (reverse oligo to PCR PGK1 promoter)

<400> SEQUENCE: 9
cgggatcctg ttttatattt gttgtaaa                                              28
```